United States Patent [19]

Morris et al.

[11] Patent Number: 5,032,111
[45] Date of Patent: * Jul. 16, 1991

[54] METHOD AND APPARATUS FOR OCULAR PERFUSION

[75] Inventors: Robert E. Morris; Clark D. Witherspoon, both of Birmingham; William E. Goggans, Jr., Pinson, all of Ala.

[73] Assignee: Vitreoretinal Development, Inc., Birmingham, Ala.

[*] Notice: The portion of the term of this patent subsequent to Feb. 13, 2007 has been disclaimed.

[21] Appl. No.: 438,170

[22] Filed: Nov. 20, 1989

Related U.S. Application Data

[63] Continuation of Ser. No. 197,567, May 23, 1988, Pat. No. 4,900,301, which is a continuation-in-part of Ser. No. 99,533, Sep. 22, 1987, Pat. No. 4,813,927.

[51] Int. Cl.⁵ .............................................. A61M 37/00
[52] U.S. Cl. ......................................... 604/23; 604/43; 604/48
[58] Field of Search ...................................... 604/22–24, 604/26–28, 30, 31, 43, 48, 49, 118, 119

[56] References Cited

U.S. PATENT DOCUMENTS 4,184,510 1/1980 Murry et al. .......................... 604/22
4,886,498 12/1989 Newton ................................ 604/118
4,900,301 2/1990 Morris et al. .......................... 604/23

FOREIGN PATENT DOCUMENTS 50507 12/1940 France ................................. 604/26

OTHER PUBLICATIONS

"Automated Regulation of Fluid Infusion Pressure During Vitrectomy", Witherspoon, M.D., et al, Arch. of Ophthalmology, vol. 104, Oct. 1986.

Primary Examiner—Stephen C. Pellegrino
Assistant Examiner—Gary Jackson
Attorney, Agent, or Firm—Jennings, Carter, Thompson & Veal

[57] ABSTRACT

Ocular perfusion during intraocular surgery of the anterior or posterior ocular cavity is optimized through the method of using a gas pump having a discernible and controllable output pressure to pressurize a reservoir of liquid infusate, which is supplied under pressure to a surgical infusion instrument for perfusion of the selected ocular chamber (Gas Forced Liquid Infusion, GFLI). The infusate selection and the infusate pressure can be controlled with a high degree of accuracy and both can be rapidly varied by audible command. Preferentially a human sensible indication of pressure is constantly available at the gas pump.

8 Claims, 3 Drawing Sheets

METHOD AND APPARATUS FOR OCULAR PERFUSION

This is a continuation of application Ser. No. 07/197,567 filed May 23, 1988, now U.S. Pat. No. 4,900,301, which is a continuation-in-part of Ser. No. 07/099,533 filed Sept. 22, 1987, U.S Pat. No. 4,813,927.

FIELD OF THE INVENTION

The present invention relates generally to apparatus and methods used in surgery conducted on the eye. More particularly, the present invention relates to apparatus used in continuous infusion processes associated with such surgery. In even greater particularity, the present invention relates to apparatus for accurately and rapidly controlling the infusion pressure of the eye and rapidly converting between liquid and gas infusion during such surgery.

BACKGROUND OF THE INVENTION

Intraoperative control of intraocular infusion pressure is an important parameter in eye surgery. Liquid pressure regulation has been accomplished in most part using gravity-fed systems involving the relative height of the infusion bottle above the eye. A discussion of the development of gas infusion may be found in "Vitreous Microsurgery" by Steven Charles, M.D. in Williams & Wilkins, 1981, volume 4. As noted therein, there are known power injectors or pumps which are capable of maintaining an accurate intraocular pressure during air infusion, as compared to manual syringe injection. Such devices have also been developed wherein a microcompressor is used to produce an inflow of gas dependent upon intraocular pressure.

As these advances are made in gas infusion apparatus, a need exist for controlled intraocular infusion method and apparatus which would facilitate the interchangeability of gas infusion and liquid infusion during surgery on the posterior segment of the eye (vitrectomy). Additionally, during surgery on the anterior chamber of the eye (cataract extraction) the need exists for more accurate, surgeon controlled and monitored liquid infusion.

During cataract surgery, the most common operation performed in the United States, the surgeon views only the anterior chamber of the eye as shown in FIG. 5, having no method of simultaneously monitoring the posterior segment.

Since the anterior chamber is quite small, containing only 0.25cc of liquid volume, small and momentary aspiration flow exceeding infusion rates will result in anterior chamber collapse, as shown in FIG. 5. The consequence of anterior chamber collapse is damage to the nonreproducible monolayer of cells (endothelium) which lines the inner surface of the cornea. Keeping it clear of fluid. This endothelial damage can then result in clouding of the cornea, with the need for subsequent cornea transplantation.

It is common for cataract surgeons to perform incomplete temporary closure of the surgical incision prior to irrigation/aspiration cataract cortex removal. A true "closed-eye" system is never achieved, and anterior chamber collapse in this condition is a sign of wound leakage of infusion liquids rather than of inadequate infusion pressure. If anterior chamber collapse is encountered, the wound should be checked for tightness.

The cataract surgeon's most common defense against perceived anterior chamber collapse is increasing of infusion pressure by raising a gravity-feed infusion bottle an estimated height above the eye as shown in FIG. 4. Note that gas is not commonly infused into the anterior chamber in such surgery. In practice, bottle height is not measured, so that actual pressure delivered to the eye is unknown, and is presumed to be sufficient when anterior chamber collapse no longer occurs.

Unfortunately, corneal endothelial damage may also occur as a result of high infusate volume or jetstream mechanical damage from the use of high flow rates under high pressure. These effects, moreover, are not readily apparent to the surgeon due to his inability to perceive the flow rate or pressure. Retinal artery occlusion may also occur, invisible to the surgeon and resulting in blindness. Finally iris prolapse through the wound may occur as a result of excessive infusion pressure.

Ideally, cataract irrigation/aspiration surgery should be performed with normal ocular pressure (25 mm Hg). Failing this, infusion pressure should be raised as little as possible to maintain anterior chamber pressure to avoid collapse during active irrigation/aspiration. Because unnecessarily high infusion pressure and flow rates can injure retinal and corneal tissues with little warning to the surgeon, increasing infusion to the eye should be the last solution attempted to remedy anterior chamber collapse. As previously stated, the surgeon should first check adequate wound closure. Further, even with an adequately closed eye, anterior chamber collapse may occur as a result of undisciplined, continuous, high rate aspirations. High vacuum aspiration is necessary to achieve cataract removal, but successful removal of blocks of cataract cortex bottle provides pressurized liquid for infusion. The gas conduit and liquid conduit are preferentially formed as a dual-tube conduit and are connected to a stopcock which allows the physician to select either gas infusion or liquid infusion.

In an alternate embodiment, adapted for anterior chamber surgery, the gas infusion line is eliminated since gas infusion is not commonly used in this type surgery; the flexible conduit connections between the liquid infusate bottle and the eye, and between the gas pressure device and the liquid infusate bottle are maintained. In both embodiments, the output of the gas pump is connected directly to the pressurized gas pocket above the infusion liquid via a conduit extending within the liquid infusion bottle

BRIEF DESCRIPTION OF THE DRAWINGS

Apparatus embodying features of our invention are depicted in the appended drawings which form a portion of this invention and wherein.

DESCRIPTION OF A PREFERRED EMBODIMENT

Figure 4:
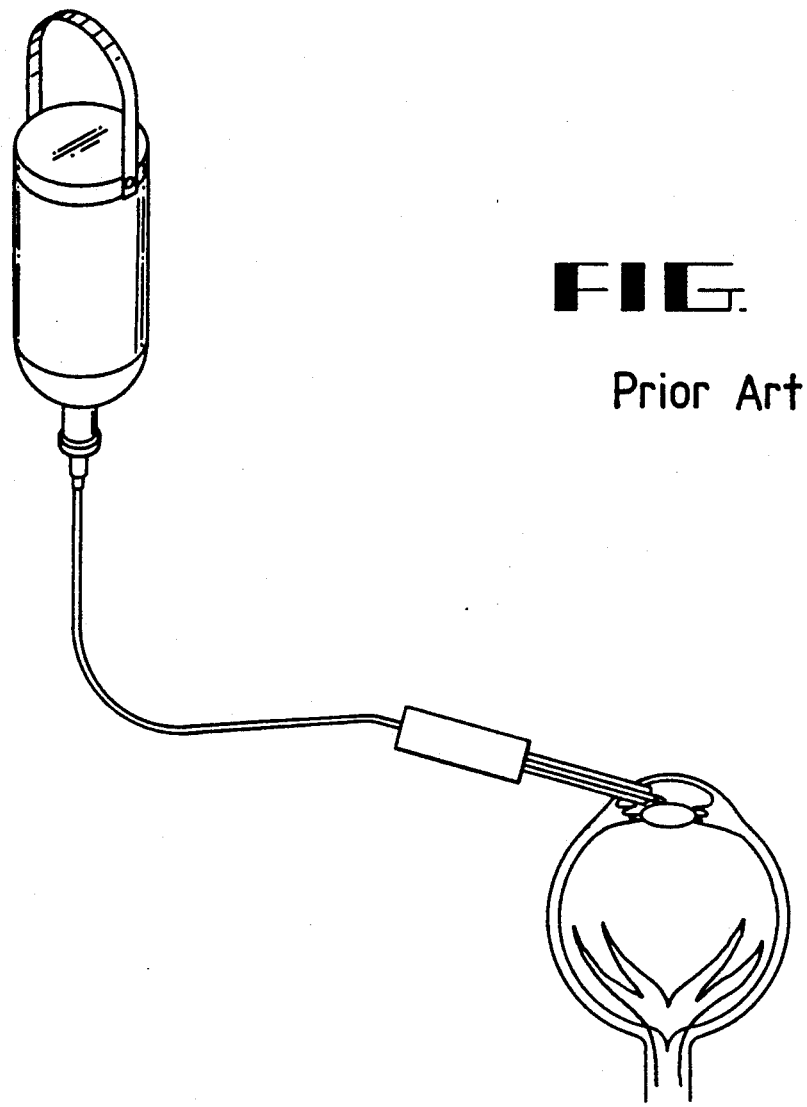
FIG. 4 shows the prior art and ocular structures.
Figure 5:
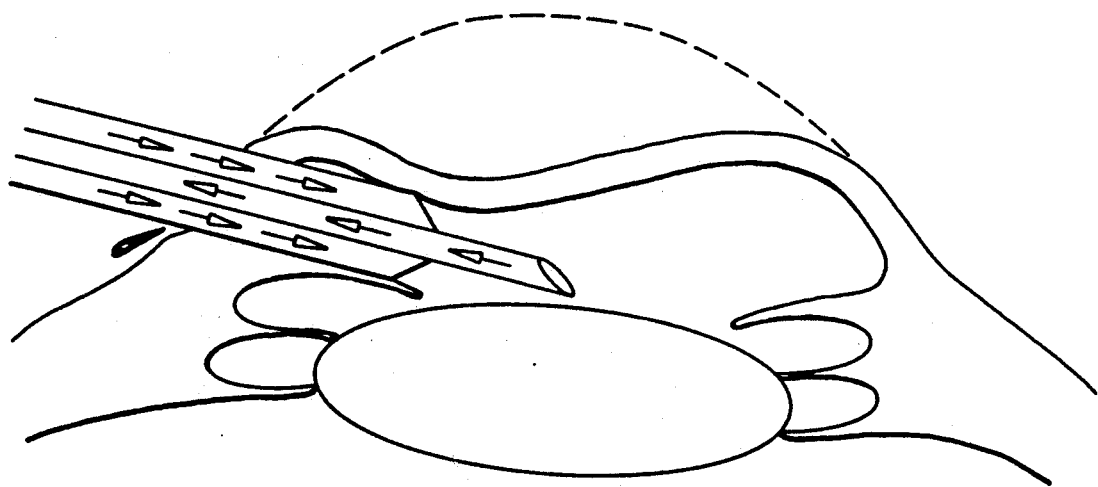
FIG. 5 shows an instance of ocular collapse.

FIG. 4 illustrates the common control methodology and apparatus for luquid infusion of the eye as heretofore used in cataract and in vitreous surgery. FIG. 5 is illustrative of common ocular collapse when using the method and apparatus shown in FIG. 4.

Referring to the figures for a better understanding of the invention, it may be seen that the invention is for use with a patient who is lying beneath surgical drapes 11 on an operating table 12. A continuous infusion air/gas pump 13 is located on an equipment stand 14 as is conventional practice. The output of the air/gas pump 13 is displayed as by LED's at digital display 16 so that the pressure generated thereby may be monitored by the surgery team and precisely controlled.

The output of the air/gas pump 13 is used to pressurize a liquid infusion bottle 23 to provide Gas Forced Liquid Infusion (GFLI) of the eye. Use of Gas Forced Liquid Infusion (with digital numeric readout of infusion pressure in view of the surgeon) allows the surgeon for the first time to accurately and continuously monitor this most important parameter. In this method, the infusion bottle is hung at eye height, so that gravity feed, the preferred technique of the prior art, contributes no pressure to perfusion/infusion. Rather, total control of perfusion pressure is instead achieved by instilling in the infusate bottle, gas under pressure, provided by the gas pump. The infusion pressure can thereby be meticulously and rapidly selected by the surgeon.

An antibacterial filter connector 17 attaches a flexible conduit 18 to the pump 13 in any conventional manner as is well known in the art. The conduit 18 extends from the equipment stand 14 to near an IV support 19 and terminates in a T-connector 21 or other suitable device for directing the airflow from the pump 13 along two paths. A fluid pressurization conduit 22 is connected between the T-connector 21 and a liquid infusion bottle which has a sealing means 25 which allows the fluid pressurization conduit to extend through the sealing means into the interior of the infusate bottle and seals the infusate bottle 23 which is 23 supported by the IV support 19 and serves to pressurize the fluid therein in accordance with the output pressure of the pump 13. This fluid pressurization conduit extends within the infusion bottle so as to connect the gas volume above liquid with the gas pump for venting purposes. A fluid delivery conduit 24 is connected as the output of infusion bottle 23 and terminates as one input to infusate stopcock selection valve 26. An air delivery conduit 27 is connected between the remaining branch of the T-connector 21 an the valve 26. Note that valve 26 may be a three-way input valve which would allow selection of either liquid, air, or finally an air/gas mixture (e.g. sulfur hexafluoride $SF_6$ 20%, perfluoropropane $C_3F_8$ 15%) delivered by a second gas pump. The valve 26 has a single output to an infusion conduit 28 which is connected to and supplies an eye infusion cannula 29.

Figure 1:
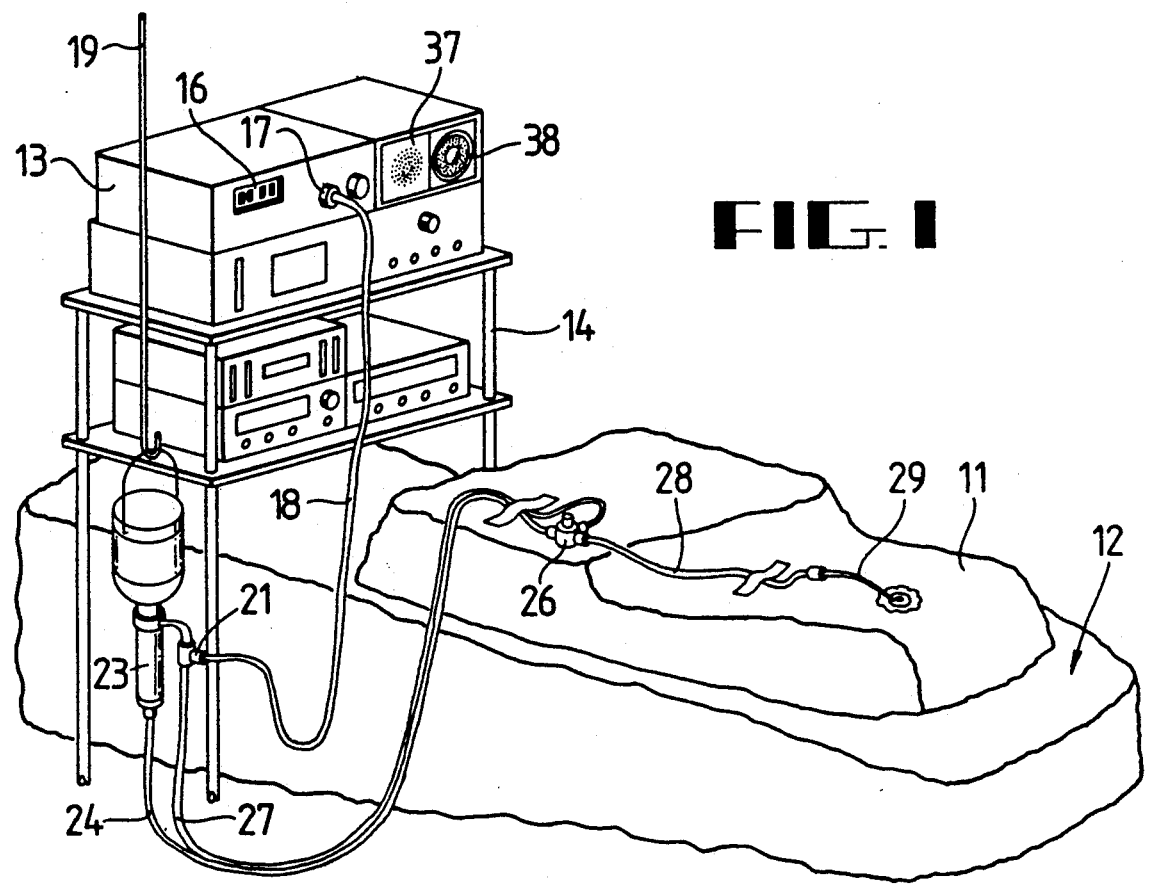
FIG. 1 is a perspective view showing the apparatus as used during surgery.

As shown in FIG. 1, the infusion bottle 23 is placed at the patient's eye level so as to contribute no gravity infusion pressure as had been customary in the prior art. Air/gas is pumped into the bottle 23 via conduits 18 and 22 to provide the desired infusion pressure. Although a normal starting pressure may be selected, it should be clear that the infusion pressure can be rapidly changed by adjusting the output pressure of the air pump 13. The air pump selected should have a digital display 16 of the pressure which should be visible to all operation room personnel. It has been determined that the displayed, conduit, and intraocular static pressures agree to within two to four mm of Hg using the present apparatus.

Valve 26 allows the surgical team to quickly switch from liquid infusion to gas infusion. Conduits 24 and 27 may be formed from the two halves of a twin plastic tube, for example Dicoc Twin Bore Silicone IV tubing, such that the valve 26 may be located immediately proximal to the short cannula 29, thereby minimizing the time and volume required to clear infusion liquid from the system cannula 29 when gas is desired.

From the foregoing, it may be seen that we have provided an effective apparatus and method (Gas Forced Liquid Infusion, GFLI) which greatly improves the surgeon's efficiency in vitrectomy operations in which liquid to gas infusion changes are desired and also provides a readily controllable means for varying the infusion pressure during all liquid infusion eye surgery including cataract removal. As is well known, it is possible to stop or reduce bleeding by raising the intraocular pressure to maximum known safe levels, usually 35 to 45 mm of Hg. Using the present invention with a digital display 16 allows the surgical team to quickly determine the infusion pressure levels and rapidly change the level as required, to maximum safe level with great accuracy.

Figure 2:
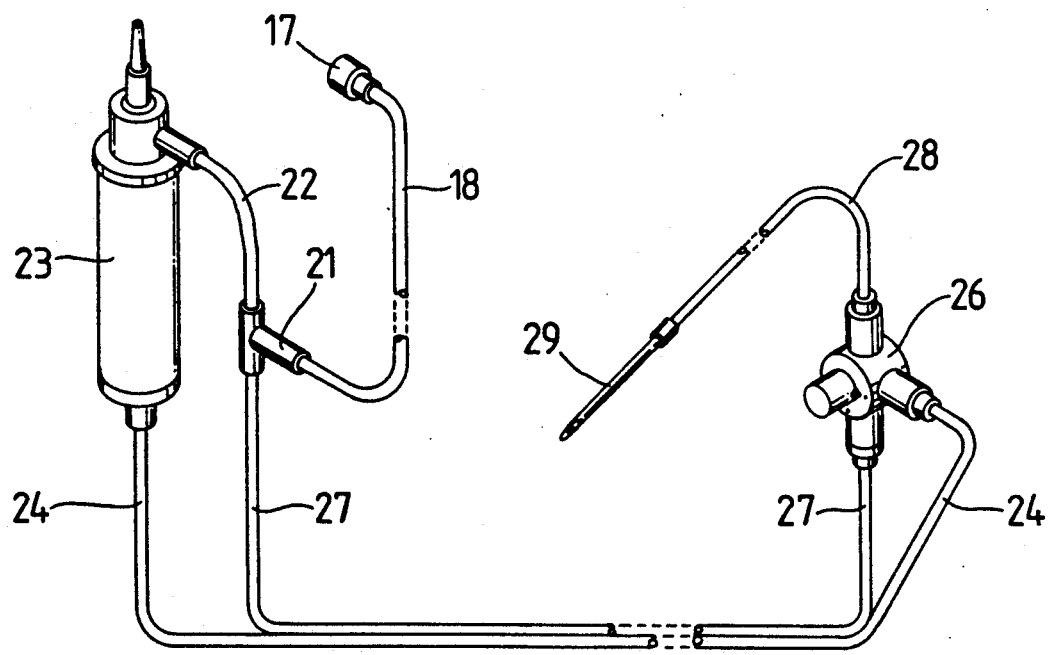
FIG. 2 is a broken lay-out view showing the invention not in use.
Figure 3:
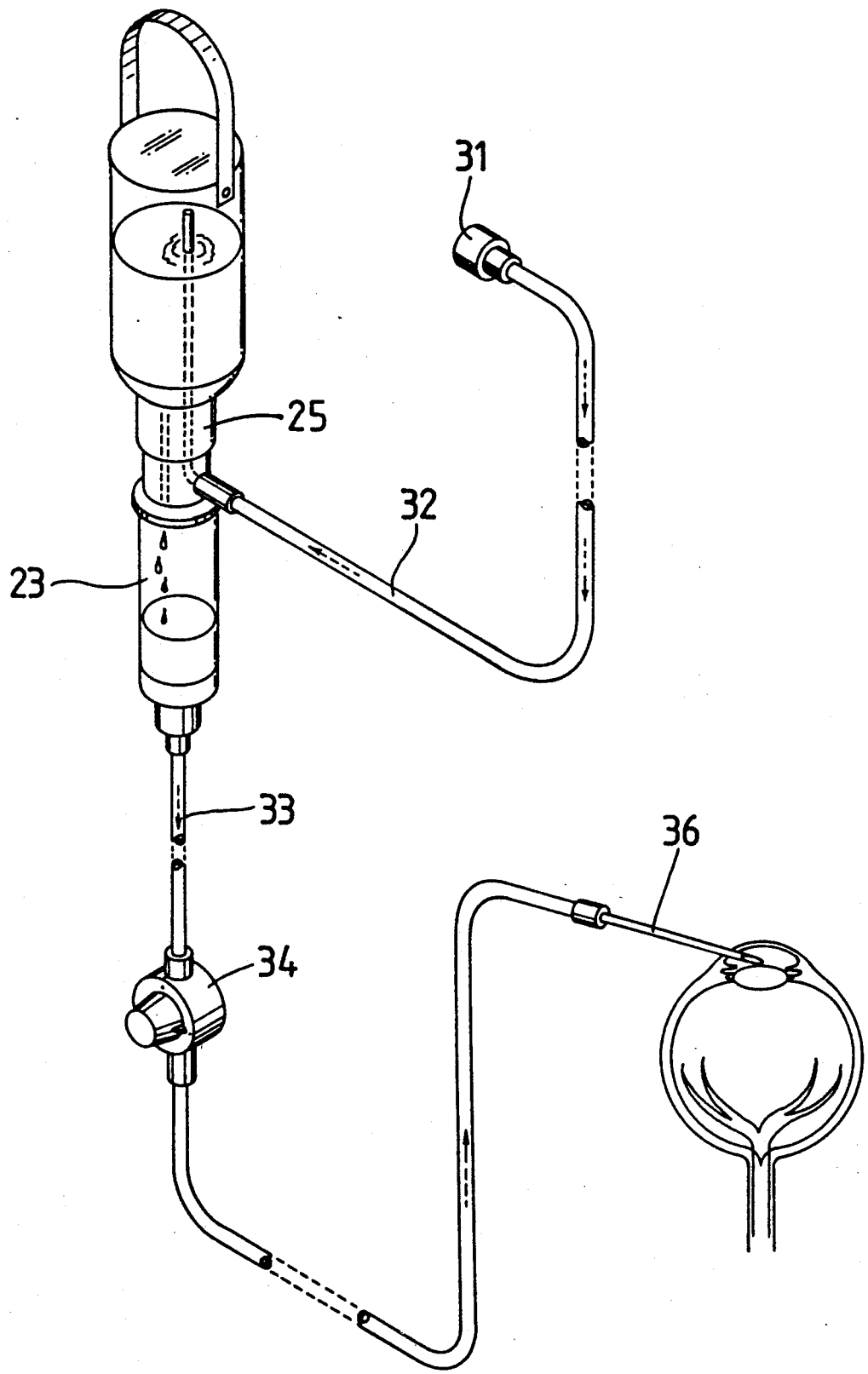
FIG. 3 is a broken lay-out view showing the cataract surgery embodiment.

It is the aspect of the invention that allows the surgical team to continuously monitor and precisely control the infusion pressure which is of critical importance to the cataract surgeon. The tubing system shown in FIG. 3 uses an antibacterial filter connector 31 to attach a flexible tubing 32 to the air pump 13. The flexible tubing 32 is connected directly to the infusion bottle 23 which is supplied with infusion liquid as shown in FIG. 2. A single flexible conduit 33 is provided to carry pressurized infusion liquid from the bottle to a valve 34 which controls the flow of liquid to the infusion/aspiration device 36 used in cataract surgery. With the digital readout 16 available the surgeon is able to constantly monitor the pressure being utilized in the eye and therefore is at all times aware of and alert to the potential deleterious consequences of overpressurization and jetstreaming. Thus, due to his ability to monitor and accurately select the intraocular pressure, the surgeon will naturally turn more attention to adequate wound closure and disciplined aspiration rather than using a potentially destructive infusion pressure level to prevent ocular collapse.

The use of the gas pump 13 to pressurize the infusion bottle 23 in either of the embodiments above also leads to a significant further refinement in the art. Voice recognition technology can be used to regulate the output pressure of the gas pump 13. Thus, an input microphone 37 is connected to a voice recognition circuit, many of which are commercially available, which in turn outputs a control signal to the pump 13. Preferentially the pump will be provided with a speaker 38 which will enunciate the pressure, subsequent to an instruction to change pressure or upon a query by the surgeon; or upon a variance of the pressure outside a predetermined tolerance. The surgeon's voice may be specifically recognized so that he might state the desired pressure in an audible voice, and the machine would respond immediately that it will seek the commanded pressure after a preset safety delay, in the absence of further commands. Infusate selector valve 26 may also be voice actuated. For the first time, perfusion pressure to the eye and infusate source can be controlled directly by the surgeon rather than necessitating the presence of other operating room personnel. Immediate pressure adjustment with voice response completes surgeon control of infusion pressure—the most vital parameter characterizing "closed-eye" surgery.

While we have shown our invention in two forms, it will be obvious to those skilled in the art that it is not so limited but is susceptible of various changes and modifications without departing from the spirit thereof.

What we claim is:

1. Apparatus for controlling the intraocular pressure during closed wound intraocular surgery consisting essentially of:
   (a) a gas pump having a variable output pressure;
   (b) a liquid infusate reservoir operatively connected to said gas pump to receive pressurized gas therefrom such that liquid infusate in said reservoir is pressurized in accordance with the output pressure of said gas pump, with said reservoir confining both said liquid infusate and a volume of gas in direct communication with said gas pump; and
   (c) an ocular surgical infusion instrument operatively connected to said liquid infusate reservoir to receive infusate therefrom.

2. A connector for use in combination with a gas pump having a variable output pressure, a gas outlet, and a liquid infusate reservoir containing an infusate, and an ocular surgical infusion instrument, comprising:
   (a) a first flexible conduit operatively connected at one end thereof to the outlet of said gas pump;
   (b) sealing means operatively connected to a second end of said first flexible conduit to provide gaseous communication between the interior of said reservoir and said first flexible conduit and for sealing said reservoir;
   (c) an infusate outlet port located in said sealing means through which liquid infusate is discharged from said reservoir; and
   (d) second flexible conduit operatively connected to said infusate outlet port at one end and in communication with said infusion instrument at a second end, wherein said first and second flexible conduits define a closed system interconnected between said gas pump and said infusion instrument.

3. A connector as defined in claim 2 further comprising an antibacterial filter operatively connected intermediate said first flexible conduit and said gas pump.

4. A connector as defined in claim 3 further comprising a valve operatively connected between said infusion instrument and said second flexible conduit for regulating the flow of infusate to said instrument.

5. A connector as defined in claim 2 wherein said first and second flexible conduits comprise lengths of flexible silicon tubing.

6. Apparatus for providing gas forced liquid infusion to a selected anterior or posterior ocular chamber comprising:
   (a) a gas pump having a variable pressure output, selectively variable over a predetermined range of pressures encountered in intraocular surgery;
   (b) a reservoir containing a liquid infusate;
   (c) a conduit member including a microbacterial filler, connected directly from the output of said gas pump to said reservoir to pressurize the liquid infusate in said reservoir;
   (d) a second conduit member operatively connected between said reservoir and an intraocular surgical instrument for delivery of the liquid infusate under pressure to the eye of a patient undergoing surgery; and
   (e) human sensible means for indicating the pressure in the eye during intraocular surgery.

7. Apparatus as defined in claim 3 wherein said human sensible means is a visible digital display showing the current output pressure of the pump.

8. A method of ocular perfusion using Gas Forced Liquid Infusion (GFLI) comprising:
   (a) supplying pressurized gas to a selected output pressure from a gas pump;
   (b) pressurizing the contents of a liquid infusate bottle with the output pressure of said gas pump;
   (c) supplying the contents of said liquid infusate bottle to a surgical infusion instrument for infusion into a selected anterior or posterior ocular chamber as infusate;
   (d) selectively varying the pressure of the infusate within the ocular chamber by controlling the output pressure of said gas pump; and
   (e) providing a human sensible indication of the pressure within the eye wherein said human sensible indicator of the output pressure is a visual signal indicating the output pressure of the pump.

* * * * *